(12) United States Patent
Coquerel et al.

(10) Patent No.: US 7,846,961 B2
(45) Date of Patent: Dec. 7, 2010

(54) α CRYSTALLINE FORM OF THE ARGININE SALT OF PERINDOPRIL, A PROCESS FOR ITS PREPARATION AND PHARMACEUTICAL COMPOSITIONS CONTAINING IT

(75) Inventors: Gérard Coquerel, Boos (FR); Loïc Lefebvre, Mont Saint Aignan (FR); Jean-Claude Souvie, Pau (FR); Pascale Authouart, Les Trois Pierres (FR)

(73) Assignee: Les Laboratoires Servier, Suresnes Cedex (FR)

( * ) Notice: Subject to any disclaimer, the term of this patent is extended or adjusted under 35 U.S.C. 154(b) by 77 days.

(21) Appl. No.: 12/224,369

(22) PCT Filed: Feb. 26, 2007

(86) PCT No.: PCT/FR2007/000335

§ 371 (c)(1),
(2), (4) Date: Nov. 10, 2008

(87) PCT Pub. No.: WO2007/099217

PCT Pub. Date: Sep. 7, 2007

(65) Prior Publication Data

US 2009/0203758 A1 Aug. 13, 2009

(30) Foreign Application Priority Data

Feb. 28, 2006 (FR) .................................. 06 01748

(51) Int. Cl.
*A61K 31/403* (2006.01)
*A61K 31/405* (2006.01)
*C07D 209/14* (2006.01)

(52) U.S. Cl. .................... 514/412; 548/492; 548/493
(58) Field of Classification Search .................. None
See application file for complete search history.

(56) References Cited

U.S. PATENT DOCUMENTS 6,696,481 B2 * 2/2004 Damien et al. .............. 514/412

FOREIGN PATENT DOCUMENTS

| EP | 0049658 | 4/1982 |
|----|---------|--------|
| WO | 01/87835 | 11/2001 |
| WO | 01/87836 | 11/2001 |
| WO | 0183439 | 11/2001 |
| WO | 03/087050 | 10/2003 |

OTHER PUBLICATIONS

Byrn et al. Solid-State Chemistry of Drugs, 2d, Chapter 11 Hydrates and Solvates/hydrates, 233-247 (1999).*
Morissette et al. Adv. Drug Delivery Rev. 2004, 56, 275-300.*
Rouhi, Chem. & Eng. News, Feb. 24, 2003, 81(8), 32-35.*
International Search Report for PCT/FR2007/000335 of Jun. 5, 2007.

* cited by examiner

Primary Examiner—Rebecca L Anderson
Assistant Examiner—Michael Barker
(74) Attorney, Agent, or Firm—Hueschen and Sage

(57) ABSTRACT

α-crystalline form of the compound of formula (I):

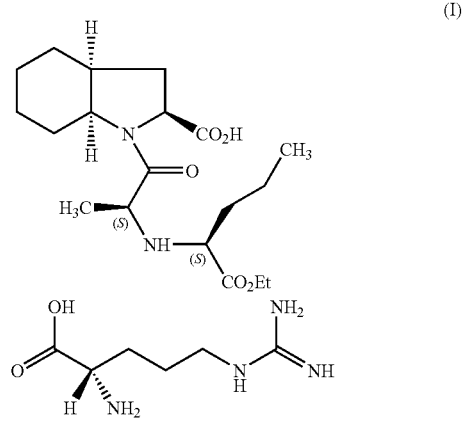

characterized by its powder X-ray diffraction diagram.

Medicinal products containing the same which are useful as inhibitors of angiotensin I converting enzyme.

9 Claims, No Drawings

α CRYSTALLINE FORM OF THE ARGININE SALT OF PERINDOPRIL, A PROCESS FOR ITS PREPARATION AND PHARMACEUTICAL COMPOSITIONS CONTAINING IT

The present invention relates to the α crystalline form of the arginine salt of perindopril of formula (I):

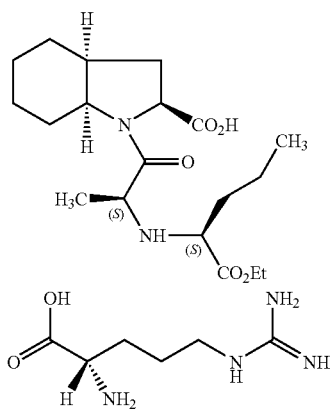

to a process for its preparation and to pharmaceutical compositions containing it.

Perindopril and its pharmaceutically acceptable salts, and more especially its arginine salt, have valuable pharmacological properties.

Their principal property is that of inhibiting angiotensin I converting enzyme (or kininase II), which allows, on the one hand, impedance of the conversion of the decapeptide angiotensin I to the octapeptide angiotensin II (a vasoconstrictor) and, on the other hand, prevention of the degradation of bradykinin (a vasodilator) to an inactive peptide.

Those two actions contribute to the beneficial effects of perindopril in cardiovascular diseases, more especially in arterial hypertension and heart failure.

Perindopril, its preparation and its use in therapeutics have been described in European Patent specification EP 0 049 658.

The arginine salt of perindopril has been described in European Patent specification EP 1 354 873.

In view of the pharmaceutical value of that compound, it has been of prime importance to obtain it with excellent stability, mainly in terms of hygroscopicity, of processability of the powder, of filterability of the solid, of grindability, and of solvent retention.

Obtaining a well-defined crystalline form allows those requirements to be met.

Patent specification EP 1 354 873 describes the arginine salt of perindopril. That document does not, however, specify the conditions for obtaining that salt in a well-defined crystalline form.

The Applicant has now found that the arginine salt of perindopril can be obtained in a well-defined crystalline form that, as a result, has valuable characteristics for filtration, drying and ease of formulation.

More specifically, the present invention relates to the α crystalline form of the compound of formula (I), characterised by the following powder X-ray diffraction peaks, measured using a diffractometer with a copper anti-cathode and expressed in terms of angle 2 theta (°): 4.5, 7.9 and 13.5.

Preferably, the present invention relates to the α crystalline form of the compound of formula (I), characterised by the following powder X-ray diffraction peaks, measured using a diffractometer with a copper anti-cathode and expressed in terms of angle 2 theta (°): 4.5, 7.9, 13.5, 17.5 and 20.6.

Even more preferably, the present invention relates to the α crystalline form of the compound of formula (I), characterised by the following powder X-ray diffraction diagram measured using a diffractometer (copper anti-cathode) and expressed in terms of inter-planar distance d, Bragg's angle 2 theta, intensity and relative intensity (expressed as a percentage of the most intense line):

| Angle 2 theta (°) | Inter-planar distance d (Å) | Intensity | Relative intensity (%) |
|---|---|---|---|
| 4.52 | 19.53 | 2211 | 88.7 |
| 7.94 | 11.12 | 2080 | 83.5 |
| 12.152 | 7.277 | 682 | 27.4 |
| 13.480 | 6.563 | 2492 | 100.0 |
| 14.029 | 6.308 | 422 | 16.9 |
| 14.948 | 5.922 | 552 | 22.1 |
| 15.873 | 5.579 | 493 | 19.8 |
| 17.531 | 5.055 | 1600 | 64.2 |
| 18.787 | 4.719 | 363 | 14.5 |
| 19.579 | 4.530 | 1078 | 43.3 |
| 20.635 | 4.301 | 1794 | 72.0 |
| 22.616 | 3.928 | 798 | 32.0 |
| 23.367 | 3.804 | 473 | 19.0 |
| 23.807 | 3.735 | 362 | 14.5 |
| 24.434 | 3.640 | 409 | 16.4 |
| 27.148 | 3.282 | 450 | 18.1 |
| 28.214 | 3.160 | 417 | 16.7 |

The invention relates also to a process for the preparation of the α crystalline form of the compound of formula (I), wherein perindopril is dissolved in water with L-arginine, and then an apolar solvent and a polar solvent are added and the crystals obtained are filtered off, washed and then dried.

Among the apolar solvents there may be mentioned, by way of example, methylcyclohexane, cyclohexane and toluene.

Among the polar solvents there may be mentioned, by way of example, dimethyl sulphoxide, N,N-dimethylformamide, N,N-dimethylacetamide and N-methyl-2-pyrrolidinone.

The crystals so obtained are in a compact form composed of baguettes.

According to one embodiment of the invention, perindopril is dissolved in water with L-arginine and then methylcyclohexane and dimethyl sulfoxide are added and the crystals obtained are filtered off, washed and then dried.

The invention relates also to pharmaceutical compositions comprising as active ingredient the α crystalline form of the compound of formula (I) together with one or more appropriate, inert, non-toxic excipients. Among the pharmaceutical compositions according to the invention there may be mentioned, more especially, those that are suitable for oral, parenteral (intravenous or subcutaneous) or nasal administration, tablets or dragées, sublingual tablets, capsules, lozenges, suppositories, creams, ointments, dermal gels, injectable preparations, drinkable suspensions.

The dosage used can be varied according to the nature and severity of the disorder, the administration route and the age and weight of the patient. It varies from 1 to 500 mg per day in one or more administrations.

The pharmaceutical compositions according to the invention may also contain a diuretic such as indapamide.

The following Examples illustrate the invention.

The powder X-ray diffraction spectrum was measured under the following experimental conditions:

Siemens D5005 diffractometer; scintillation detector;
Copper anti-cathode, voltage 40 KV, intensity 30 mA;
Mounting θ-θ, fixed specimen;
Temperature: ambient;
Measurement range: 3° to 30°;
Increment between each measurement: 0.04°;
Measurement time per step: 4 s;
Fixed slits: 1.6 mm;
Kβ filter (Ni);
No internal reference;
Zeroing procedure using Siemens slits;
Experimental data processed using EVA software (version 9.0).

EXAMPLE 1

α Crystalline Form of Perindopril Arginine Salt 1.5 kg of water, 328 g of perindopril and 155 g of L-arginine are introduced into a reactor at ambient temperature and with stirring. When a clear solution is obtained, 630 g of methylcyclohexane are added, and then 4.7 kg of dimethyl sulphoxide are added slowly. The mixture is then stirred until the temperature of the heterogeneous mixture stabilises at around 20.0° C., after which the mixture is filtered and the solid obtained is washed and dried.

The crystals so obtained are in a compact form composed of baguettes.

The water content of the resulting product is approximately 3.2%, which corresponds to a monohydrate.

Powder X-ray Diffraction Diagram.

The powder X-ray diffraction profile (diffraction angles) of the α form of perindopril arginine salt is given by the significant lines collated in the following table together with the intensity and relative intensity (expressed as a percentage of the most intense line).

| Angle 2 theta (°) | Inter-planar distance d (Å) | Intensity | Relative intensity (%) |
|---|---|---|---|
| 4.52 | 19.53 | 2211 | 88.7 |
| 7.94 | 11.12 | 2080 | 83.5 |
| 12.152 | 7.277 | 682 | 27.4 |
| 13.480 | 6.563 | 2492 | 100.0 |
| 14.029 | 6.308 | 422 | 16.9 |
| 14.948 | 5.922 | 552 | 22.1 |
| 15.873 | 5.579 | 493 | 19.8 |
| 17.531 | 5.055 | 1600 | 64.2 |
| 18.787 | 4.719 | 363 | 14.5 |
| 19.579 | 4.530 | 1078 | 43.3 |
| 20.635 | 4.301 | 1794 | 72.0 |
| 22.616 | 3.928 | 798 | 32.0 |
| 23.367 | 3.804 | 473 | 19.0 |
| 23.807 | 3.735 | 362 | 14.5 |
| 24.434 | 3.640 | 409 | 16:4 |
| 27.148 | 3.282 | 450 | 18.1 |
| 28.214 | 3.160 | 417 | 16.7 |

EXAMPLE 2

Pharmaceutical Composition

Preparation formula for 1000 tablets each containing 4 mg of active ingredient:

| | |
|---|---|
| Compound of Example 1 | 4 g |
| Hydroxypropylcellulose | 2 g |
| Wheat starch | 10 g |
| Lactose | 100 g |
| Magnesium stearate | 3 g |
| Talc | 3 g |

The invention claimed is:

1. An α-crystalline form of the L-arginine salt of perindopril of formula (I):

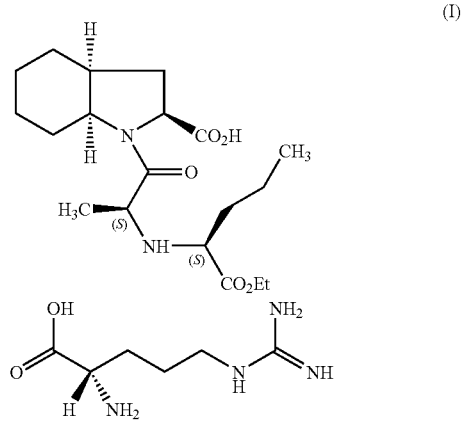

(I)

exhibiting essentially the following powder X-ray diffraction peaks, measured using a diffractometer with a copper anti-cathode and expressed in terms of Bragg's angle 2 theta (°): 4.5, 7.9 and 13.5.

2. The α-crystalline form of the compound of formula (I) according to claim 1, characterised by the following powder X-ray diffraction peaks, measured using a diffractometer with a copper anti-cathode and expressed in terms of Bragg's angle 2 theta)(°): 4.5, 7.9, 13.5, 17.5 and 20.6.

3. The a-crystalline form of the compound of formula (I) of claim 1, exhibiting essentially the following powder X-ray diffraction diagram measured using a diffractometer (copper anticathode) and expressed in terms of inter-planar distance d, Bragg's angle 2 theta, intensity and relative intensity (expressed as a percentage of the most intense line):

| Angle 2 theta (°) | Inter-planar distance d (Å) | Intensity | Relative intensity (%) |
|---|---|---|---|
| 4.52 | 19.53 | 2211 | 88.7 |
| 7.94 | 11.12 | 2080 | 83.5 |
| 12.152 | 7.277 | 682 | 27.4 |
| 13.480 | 6.563 | 2492 | 100.0 |
| 14.029 | 6.308 | 422 | 16.9 |
| 14.948 | 5.922 | 552 | 22.1 |
| 15.873 | 5.579 | 493 | 19.8 |
| 17.531 | 5.055 | 1600 | 64.2 |
| 18.787 | 4.719 | 363 | 14.5 |
| 19.579 | 4.530 | 1078 | 43.3 |

-continued

| Angle 2 theta (°) | Inter-planar distance d (Å) | Intensity | Relative intensity (%) |
|---|---|---|---|
| 20.635 | 4.301 | 1794 | 72.0 |
| 22.616 | 3.928 | 798 | 32.0 |
| 23.367 | 3.804 | 473 | 19.0 |
| 23.807 | 3.735 | 362 | 14.5 |
| 24.434 | 3.640 | 409 | 16.4 |
| 27.148 | 3.282 | 450 | 18.1 |
| 28.214 | 3.160 | 417 | 16.7 |

4. A process for the preparation of the α-crystalline form of the compound of formula (I) of claims 1, wherein perindopril is dissolved in water with L-arginine, and an apolar solvent and a polar solvent are added, wherein the apolar solvent is selected from methylcyclohexane, cyclohexane and toluene, and the polar solvent is selected from dimethyl sulphoxide, N,N-dimethylformamide, N,N-dimethylacetamide and N-methyl-2-pyrrolidinone, and the crystals obtained are filtered off, washed and dried.

5. The process of claim 4, wherein the apolar solvent is methylcyclohexane and the polar solvent is dimethyl sulphoxide.

6. A pharmaceutical composition comprising as active ingredient the compound of claim 1, in combination with one or more pharmaceutically acceptable, inert, non-toxic carriers.

7. The pharmaceutical composition of claim 6, further comprising a diuretic.

8. The pharmaceutical composition of claim 7, wherein the diuretic is indapamide.

9. A method for treating arterial hypertension and heart failure, comprising the step of administering to a living animal body, including a human, a therapeutically effective amount of the compound of claim 1.

* * * * *

UNITED STATES PATENT AND TRADEMARK OFFICE
CERTIFICATE OF CORRECTION

| | |
|---|---|
| PATENT NO. | : 7,846,961 B2 |
| APPLICATION NO. | : 12/224369 |
| DATED | : December 7, 2010 |
| INVENTOR(S) | : Gerard Coquerel et al. |

It is certified that error appears in the above-identified patent and that said Letters Patent is hereby corrected as shown below:

Column 4, Line 47: "angle 2 theta)" should be -- angle 2 theta --.

Signed and Sealed this
Tenth Day of May, 2011

David J. Kappos
*Director of the United States Patent and Trademark Office*